(12) United States Patent
Hochman (10) Patent No.: US 7,896,833 B2
(45) Date of Patent: Mar. 1, 2011

(54) COMPUTER CONTROLLED DRUG DELIVERY SYSTEM WITH DYNAMIC PRESSURE SENSING

(75) Inventor: Mark N. Hochman, Great Neck, NY (US)

(73) Assignee: Milestone Scientific, Inc, Livingston, NJ (US)

( * ) Notice: Subject to any disclaimer, the term of this patent is extended or adjusted under 35 U.S.C. 154(b) by 0 days.

(21) Appl. No.: 12/552,723

(22) Filed: Sep. 2, 2009

(65) Prior Publication Data

US 2009/0326482 A1    Dec. 31, 2009

Related U.S. Application Data

(62) Division of application No. 11/614,471, filed on Dec. 21, 2006, now Pat. No. 7,618,409.

(51) Int. Cl.
*A61M 31/00* (2006.01)
(52) U.S. Cl. .......................... 604/65; 604/246
(58) Field of Classification Search ............. 604/65–67, 604/131, 151, 93.01, 246, 890.1
See application file for complete search history.

(56) References Cited

U.S. PATENT DOCUMENTS

| 4,747,824 A * | 5/1988 | Spinello ................... 604/512 |
| 5,180,371 A * | 1/1993 | Spinello ................... 604/118 |
| 5,954,701 A * | 9/1999 | Matalon ................... 604/272 |
| D422,361 S * | 4/2000 | Herbst et al. ............... D24/176 |
| D423,665 S * | 4/2000 | Herbst et al. ............... D24/111 |
| D427,314 S * | 6/2000 | Herbst et al. ............... D24/176 |
| 6,132,414 A * | 10/2000 | Herbst et al. ............... 604/403 |
| 6,152,734 A * | 11/2000 | Herbst et al. ............... 433/82 |
| 6,200,289 B1 * | 3/2001 | Hochman et al. ............. 604/67 |
| 6,296,623 B2 * | 10/2001 | Spinello ..................... 604/118 |
| 6,652,482 B2 * | 11/2003 | Hochman ..................... 604/65 |
| 6,786,885 B2 * | 9/2004 | Hochman et al. ............. 604/67 |
| 6,887,216 B2 * | 5/2005 | Hochman et al. ............. 604/67 |
| 6,945,954 B2 * | 9/2005 | Hochman et al. ............. 604/67 |
| 2004/0215080 A1 * | 10/2004 | Lechner ...................... 600/463 |
| 2005/0004514 A1 * | 1/2005 | Hochman ..................... 604/67 |
| 2006/0102174 A1 * | 5/2006 | Hochman ............. 128/200.23 |
| 2006/0122555 A1 * | 6/2006 | Hochman ..................... 604/67 |

* cited by examiner

*Primary Examiner*—Theodore J Stigell (57) ABSTRACT

Apparatus administers dental anesthetic to intraligamentary tissue with a drive unit and handpiece with injection needle connected by flexible tube to the unit. The drug is passes to the tissue at an instantaneous pressure at the needle tip that varies due to placement. A minimum threshold pressure is desired for administering the drug to the tissue. A practitioner moves the handpiece to insert the needle tip near the intraligamentary tissue and the instantaneous pressure is sensing or calculating. An auditory ascending signal indicates when the instantaneous pressure is rising, and when the instantaneous pressure reaches the threshold pressure a perceptible auditory specific signal indicates the practitioner has moved the tip into intraligamentary tissue. The tip is then maintained for supplying a selected dosage of the drug. Another auditory signal notifies the practitioner that the instantaneous pressure is declining or fluctuating before reaching the minimum threshold pressure.

4 Claims, 3 Drawing Sheets

COMPUTER CONTROLLED DRUG DELIVERY SYSTEM WITH DYNAMIC PRESSURE SENSING

CROSS-REFERENCE TO RELATED APPLICATION

This is a divisional of U.S. patent application Ser. No. 11/614,471 file Dec. 21, 2006 which is now U.S. Pat. No. 7,618,409 issued Nov. 17, 2009, and which is incorporated herein by reference.

FIELD AND BACKGROUND OF THE INVENTION

The present invention relates in general to drug delivery systems, and, in particular, to a new and useful apparatus and method for the delivery of a drug to a subject through a needle.

Published U.S. Patent Application US 2006/0122555 entitled Drug Infusion Device . . . , is incorporated here by reference and is owned by the assignee of the subject application, Milestone Scientific Inc., and is invented by the current inventor. This application is not prior art to the subject application but discloses an actuator with a mechanism for sensing and for feeding back the reaction force being experienced by a shaft being displaced by the actuator, for regulating activation of the actuator in response to the reaction force.

U.S. Published Patent Application 2004/0215080 to Lechner is incorporated here by reference for its teaching of a device for locating an anatomical cavity in the body. This reference is interesting for its use of a continuous audible signal that indicates the pressure of a fluid in a reservoir that is meant to be injected into the body of a subject through a needle. When the sought cavity has been reached by the needle, the audible signal indicates a corresponding pressure drop in the reservoir to the operator. Fluid pressure in the reservoir and not at the needle point is measured and used in this published patent application. There is no teaching or suggestion of the correlation between tissue type and a minimum or desired threshold pressure, nor the importance of taking or calculating the needle tip pressure.

Other important differences between the Lechner application and the present invention are illustrated in paragraph [0035] of the image version of the Lechner application where it is stated that: "calibration of the pressure-measurement is not critical, since the user is working on the basis of changes which he detects in the sound signal." Lechner uses a relative scale to determine identification of "cavity" or structure. In paragraph [0063] Lechner goes on to expand the use of the device to "locate a region" or "tumor in the body of a person" based on the observation that a tumor generally has different properties from the surrounding tissue, thus teaching the importance of a relative pressure change in which it is situated, and in particular the tumor will present a different resistance to the penetration of a fluid as compared to the surrounding tissue.

The Lechner device thus requires the detection of a relative change in pressure to differentiate and discriminate from the surroundings. It is therefore a system based on relative change, hence the need to provide a continuous acoustic feedback otherwise the user would miss the relative change. The Lechner device cannot identify any specific tissue based on absolute value of pressure, but can only differentiate when there is a substantial change in a relative pressure.

U.S. Pat. No. 6,200,289 which was co-invented by the inventor of the subject application, its related U.S. Pat. Nos. 6,786,885; 6,945,954; and 6,887,216; as well as its related U.S. Published Patent Applications 2005/0004514; 2006/0102174; and 2006/0122555, which are all incorporated here by reference, disclose and claim devices that control the exit pressure for a fluid being injected into a patient.

A handpiece and system marketed by the assignee of the subject application under the registered trademark THE WAND, can be used to administer drugs in general, and dental anesthetic in particular. This handpiece and other aspects of the overall system for administering anesthetics in a controlled manner with reduced pain to the subject, are disclosed and claimed in U.S. Pat. Nos. 4,747,824; 5,180,371; D422,361; D423,665; D427,314; 6,132,414; 6,152,734; and 6,652,482; which are also all incorporated here by reference.

U.S. Pat. No. 6,296,623 discloses a needle handle and anesthetic carrier assembly for delivering anesthetic under pressure to a patient and U.S. Pat. No. 6,629,958 discloses a hypodermic needle structure which can be used, for example, for administering a periodontic ligament (PDL) injection, which is also referred to as an intraligamentary injection.

The PDL is where the gingival tissue meets the tooth across a thin band of ligament that connects the tooth to the bone. This injection, however, is notoriously difficult to administer properly and is often painful to the patient due to various factors, including the extreme hardness or high-density of PDL tissue.

The periodontal ligament injection technique was first described in the early 1900's by Doctors Guido Fischer and Cassamani. The technique utilized a standard dental syringe and a "blind" placement of the hollow-bore metal needle into the gingival sulcus, and advancing the needle into the periodontal ligament located between the root surface (cementum) and the bony socket of a tooth. Once the needle was in the periodontal ligament, the clinician generated maximum pressure on the standard dental syringe or on a high-pressure pistol-grip lever syringe. The total recommended volume of anesthetic solution was 0.2 ml to 0.4 ml using this method.

Critical to the technique was the placement of the needle tip within or at the entrance to the periodontal ligament as well as the generation of high pressure or typically between 600-1200 psi to drive anesthesia into this dense tissue. Both of these features of the technique have significant pitfalls. Authors over the past century have described the difficulties of proper needle position within the desired location because of the obvious lack of direct visualization and identifiable anatomic landmarks, hence a "blind" approach to needle placement. In addition to placement of the needle tip, maintaining correct placement during administration is difficult to achieve and to confirm.

Applying maximum hand-pressure on the dental syringe generates extreme high pressures. Although advocated to forcibly move anesthetic solution through the dense tissues, unusually high syringe pressures cause tissue damage as evidenced by histologic, animal and human studies that have repeatedly demonstrated the adverse tissue reactions from the use of such high pressures. This tissue damage results in subjective pain perception reported by dental patients when the intraligamentary or PDL injection is performed using a traditional technique and mechanical dental syringe.

In addition to the needle placement issues and problems with high pressure in tissues, traditional syringes do not allow the clinician to confirm that the correct amount of anesthesia has been delivered, as both blockage and/or leakage during injection can occur. Due to these difficulties, the previous technique can lead to insufficient duration of anesthesia. Workers in the field have reported a 10 to 20 minute duration of effective pulpal anesthesia for the PDL technique that they tested. Their research used a variety of local anesthetics with varying concentrations of vasoconstrictors. When performed with greater volume, the PDL technique demonstrated a longer effective working time correlated with a larger dosage administered. Limited anesthetic solution volumes result in limited duration of anesthesia.

These traditional techniques and technologies utilized in routine intraligamentary injections, are thus hampered by the blind nature of the injection, the extreme pressures generated in local tissues during the procedure, and the relatively small volume of anesthesia that is reliably delivered. These factors have resulted in a reduced duration of anesthesia and increased pain associated with tissue damage.

A need exists for an improved apparatus and method for injecting a drug into selected tissues of a subject with increased control and, importantly, increased feedback information to the practitioner who is administering the injection.

SUMMARY OF THE INVENTION

It is an object of the present invention to provide an apparatus and method for the controlled injection of a drug into a selected tissue of a subject by a practitioner, which comprises: a drive unit for supplying a drug at, at least one flow rate; a handpiece for being held by the practitioner, the handpiece being connected to the drive unit for receiving the drug and being adapted for holding an injection needle to be inserted into the selected tissue of the subject by the practitioner, for passing the drug to the selected tissue at an instantaneous absolute pressure that varies as a function of the type of the selected tissue being injected, and a placement of the needle in the tissue, there being a minimum, threshold or desired absolute pressure which is preferred for administering the drug to the selected tissue; a pressure sensor for sensing or for calculating the instantaneous absolute pressure; and a feedback mechanism for supplying a perceptible signal to the practitioner that indicates when the instantaneous pressure has reached the minimum pressure, to guide movement of the placement of the needle by the practitioner at least until the minimum pressure has been reached.

The perceptible signal may be audible, or visual, or both. For example, the audible signal may have a pitch and/or a volume that increases with pressure, to a set point or to a point when a different audible sound is generated that indicates the desired minimum, desired or optimum pressure has been reached. The visual signal may be a rising scale on the drive unit or a numeric readout or both, and may be used in addition to the audible signal or alone. The signal may even be of another type, such as tactile signal, e.g. generated by a vibrating member that is in contact with the practitioner and which has a vibration that increases in frequency and/or amplitude as pressure increases to the desired point, when the tractile signal can also change to indicate that the desired pressure has been reached.

Accordingly, another object of the invention is to provide an apparatus and method that will return a feedback signal to the practitioner as he or she inserts and positions the needle in the selected tissue, to guide the movement of the needle in real time and with quantified information corresponding to the instantaneous fluid pressure of the drug at the tip of the needle being constantly supplied to the practitioner.

Another object of the present invention is to provide an apparatus and method which, for the first time, allows a practitioner to reliably perform single tooth anesthesia (i.e. Intraligamentary injection a.k.a. periodontal ligament or PDL). The apparatus provides continuous monitoring of the exit-pressure in real-time, here called the instantaneous pressure, during all phases of drug administration. The invention also has the ability to limit the maximum pressure used and detects loss of pressure from leakage during an injection.

An important and critical aspect of using pressure sensing technology according to the present invention, is being able to accurately identify specific tissue types based on real-time measurements of tissue resistance, i.e. tissue compliance and interstitial tissue pressure. Pressure measurement of different tissue-density type is related to the physical compliance of a specific tissue during fluid injection. Compliance is defined as the ratio of increase (change) of volume to the simultaneous increase (change) in fluid pressure.

The dynamic pressure sensing capability of the apparatus of the invention is a means of measuring tissue compliance to accurately identify specific tissue type. This attribute sets this technology apart from previous drug delivery systems whether they are manual dental syringes or first-generation computerized delivery systems.

The ability to accurately identify specific tissue types based on dynamic pressure measurements has been published in both the medical and dental literature but no device has been developed until now to take advantage of this relationship.

See for example Ghelber O, Gebhard R, Adebayo G, Szmuk P, Hagberg C, Ianucci D.: *Utilization of the Compu-Flo™ in determining the pressure of the epidural space: a pilot study*. Anesth Analg 2005:100:S-189. In this study Ghelber et al. demonstrated the ability to differentiate between specific tissue types during a subcutaneous injection based on pressure.

The subject inventor, Mark Hochman, and co-workers, performed 200 dental injections that demonstrated the ability to identify three specific tissue type categories that were based on interstitial pressure measurements in the intra-oral cavity, namely the periodontal ligament tissue, the attached gingival, and the unattached gingiva mucosa (Hochman M, Friedman M, Williams W, Hochman C.: *Interstitial tissue pressure associated with dental injections: A clinical study*. Quintessence Int. 2006; 37:469-476).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Hardware Overview

Figure 2:
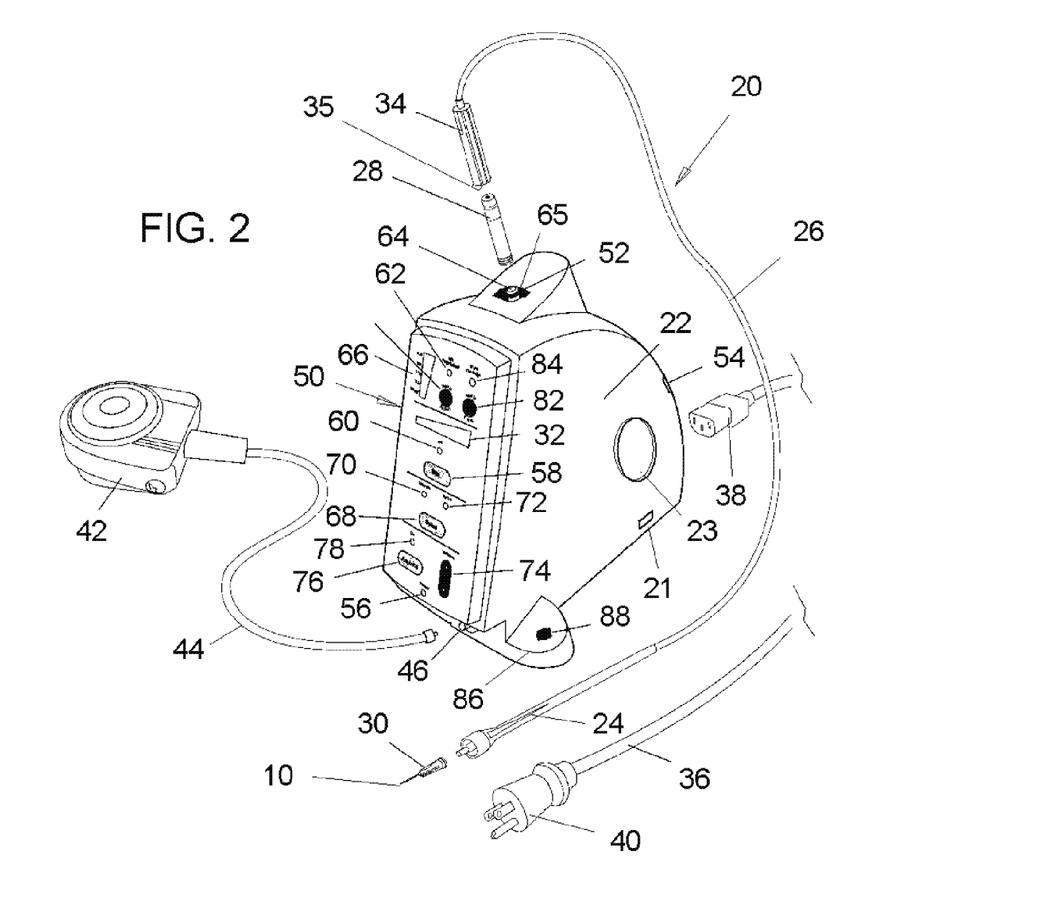
FIG. 2 is a perspective view of a preferred embodiment of the apparatus of the present invention.

Referring now to the drawings, in which like reference numerals are used to refer to the same or similar elements, FIG. 2 shows an apparatus generally designated 20, for a controlled injection of a drug into a selected tissue of a subject by a practitioner, comprising a drive unit 22 for supplying the drug at, at least one flow rate and a handpiece handle 24 for being held by the practitioner, the handpiece being connected by a flexible tube or hose 26 to the drive unit 22 for receiving the drug from a known dental anesthetic cartridge 28 that is engaged to the drive unit.

Micro-bore tubing 26 has a preferred OD (outside diameter) of 0.078"+/−0.002" and in preferred ID (inside diameter) of 0.013"+/−0.002" with an 80 durometer material hardness which is Alpha 222R polymer for example. Other materials may be used as would be know by those skilled in the art. In the past 70 durometer tubing has been used. The tubing durometer and ID can be important as well as the tubing OD as these attributes can effect performance in some way. A preferred range for OD is about 0.05 to 0.10", or preferably about 0.07 to 0.09". A preferred range for ID is about 0.008 to 0.030" or preferably about 0.010 to 0.017". A preferred range for durometer hardness is about 60 to 90, or preferably about 65 to 85.

Figure 4:
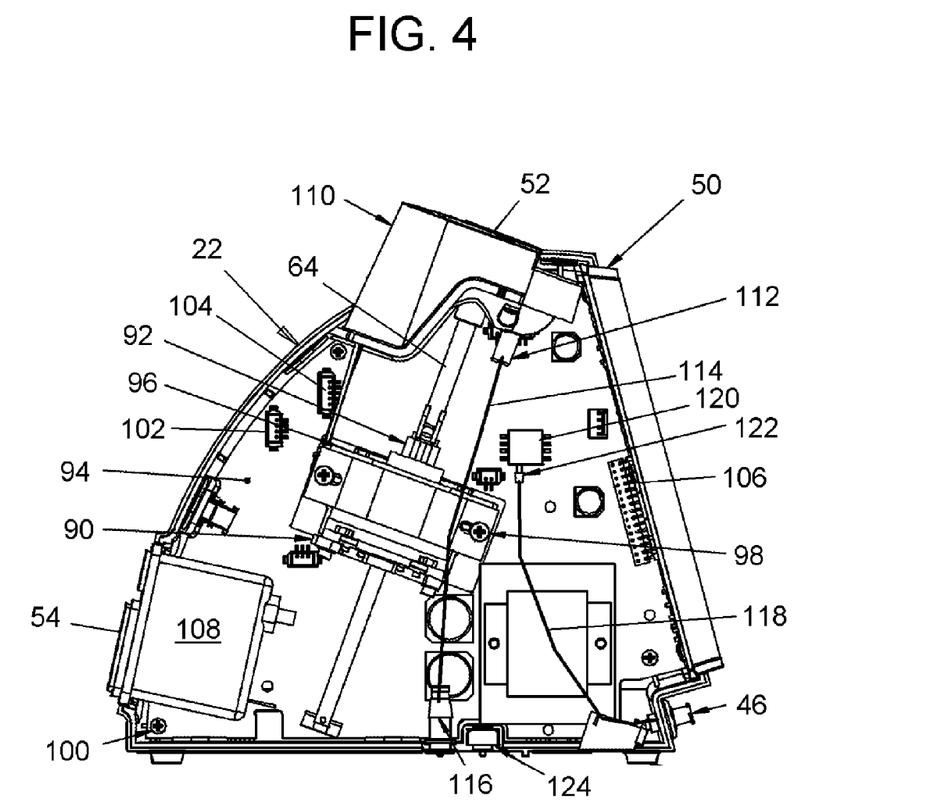
FIG. 4 is a side elevational view of the drive unit with its left housing part removed to reveal its interior structures.

Turning now to FIG. 4, a pressure sensor or calculator unit 90 mounted to a linear plunger motor assembly 92 inside drive unit 22, for example, of the type disclosed in U.S. Patent Application US 2006/0122555, senses or calculates this instantaneous absolute pressure at the needle tip or point, and a feedback mechanism such as an audible sound supplied by a sound generator such as a speaker 23 in unit 22, or a visual display such as a lighted scale 32, supplies a perceptible signal to the practitioner.

Turning now to FIG. 4, a pressure sensor or calculator unit 90 mounted to a linear plunger motor assembly 92 inside drive unit 22, for example, of the type disclosed in U.S. Patent Application US 2006/0122555, senses or calculates this instantaneous absolute pressure at the needle tip or point, and a feedback mechanism such as an audible sound supplied by a speaker 23 in unit 22, or a visual display such as a lighted scale 32, supplies a perceptible signal to the practitioner.

This signal is designed to be indicative of the instantaneous pressure, for example, as the instantaneous pressure increases, the audible tone increases in pitch and/or volume and the lights of the visual scale 32 light up, first at its smaller end to the left in FIG. 2, and then incrementally toward its larger end to the right. This signals the practitioner that his or her manipulation and guiding of the needle tip or point 10 into the selected tissue is advantageously increasing the instantaneous pressure for the liquid drug at the needle tip 10. The perceptible signal may alternatively only provide a signal that indicates when the instantaneous pressure has reached the minimum desired pressure. At this point the tone sounds for the first time, or, if it has been changing as the pressure has been increasing, the tone changes in a recognizable manner, e.g. a jump in pitch or volume or both, to indicate to the practitioner that his or her movement of the needle has succeeded in attaining the minimum pressure so that proper and sufficient dosing of the selected tissue with the drug, can be achieved. The visual signal, e.g. in the form of the increasingly lit scale 32 or even a digital readout, may also show the pressure as it increases toward the desired pressure, a fully lit scale 32 indicating that the desired pressure has been reached.

Returning to FIG. 4, motor assembly 92 is mounted to a main component board 94 in unit 22 and held in place by a bracket 96 and screws 98. Board 94 is mounted in unit 22 by screws 100 and also carried the computer elements 102, 104 and 106 for performing the various functions of the drive unit such as activating the motor assembly 92 to move the plunger 64, driving the speaker, calculating the absolute pressure at the needle tip and other functions described here. Power is supplied by a power module 108 that carried the power switch 54 and socket 52 is carried by a cassette assembly 110 through which plunger 64 can move and to which the cartridge holder 34 is attached.

In case the cassette assembly 110, which is a hermetically sealed assembly, leaks for any reason, it includes an upper drain fitting 112 that is connected by a schematically shown hose 114 to a lower drain fitting 116 that opens downwardly to discharge the leaked liquid below the unit. This avoids the danger of leakage into the delicate, electronic workings of drive unit 22 and the resulting damage.

As well be explained in greater detail later a foot control receptacle 46 is connected by and air hose schematically shown at 118 to an air fitting 122 of an air switch 120 that has multiple activation positions.

At the bottom of the unit 22, near the drain 116 a standard captured mounting screw 124 is provided for mounting the unit on a stand, tripod, arm or the like. This is the same type of standard quarter inch mount screw used on camera mounts so that any standard tripod screw will fit. This is intended to allow the unit of the invention to be mounted and affixed to a support arm or pole. It could also be used to secure the unit to a table top or counter-top.

A USB port 21 is also available for uploading and/or displaying the instantaneous pressure readings on and to a personal computer or other computer suitably programmed to accumulate the pressure information and record each injection performed with a time code so that useful information can be accumulated for future study. USB port 21 may also be used be used for remote display to show graphic representation and data of injection. The USB port is also to serve as a convenient means for recording data to document the injection event. Patient identification information can be input to secure a record that can be reviewed at a later time.

Although the principles of the invention can be used for a wide variety of tissues and drugs, the inventor has extensively confirmed the usefulness of the invention on a single tooth anesthesia, intraligamentary (PDL) injection technique.

The Intraligamentary Injection:

The single tooth anesthesia, intraligamentary or PDL injection technique of the present invention differs substantially from the prior art procedure primarily in that it uses real-time dynamic pressure sensing feedback to both locate the ligament and ensure the proper functioning of the device. In addition, it uses a precise flow-rate (e.g. 0.005 ml/sec for a PDL injection) and controlled "moderate" desired, minimum or threshold absolute pressure (e.g. preferable 250 to 450 psi for the PDL injection, or even up to the range of 200 to 500 psi) for the delivery of anesthesia.

Figures 1, 3:
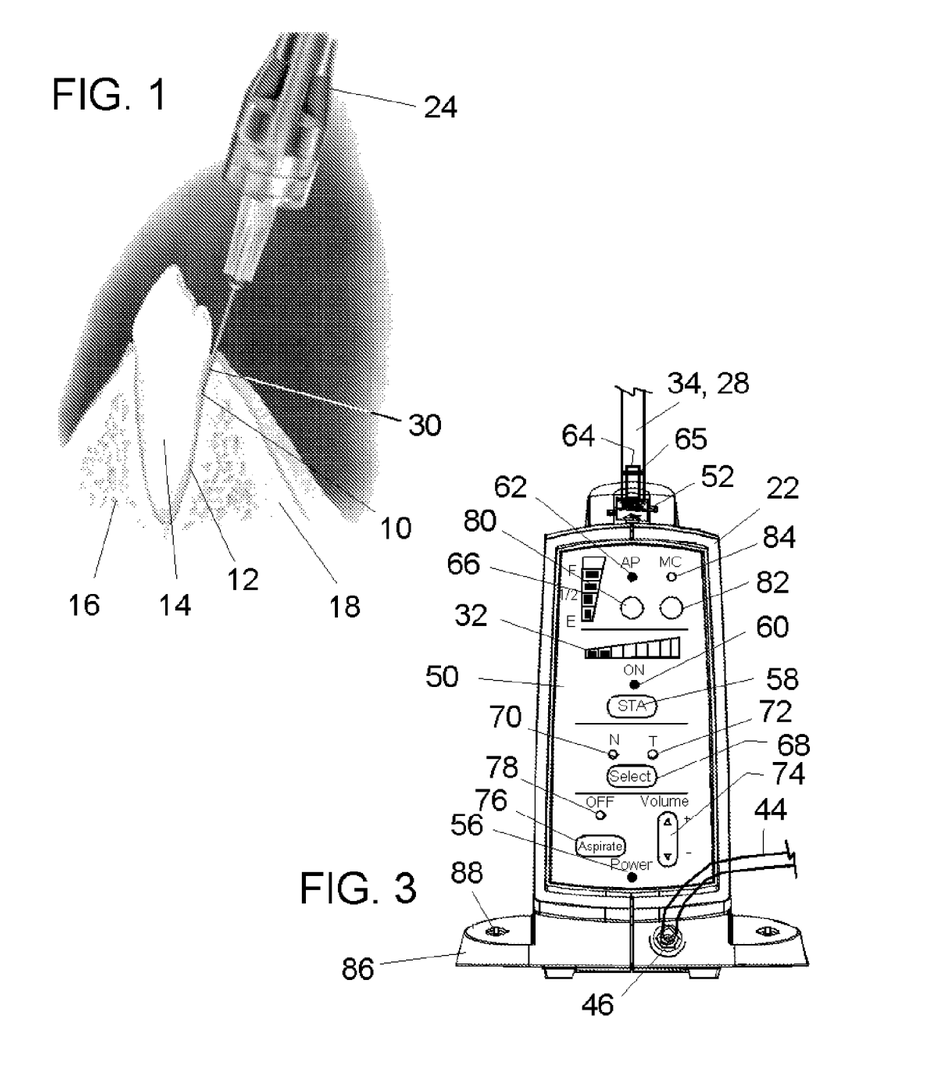
FIG. 1 is a cross-sectional view of a subject's tooth showing an initial placement of a needle for a PDL, single tooth anesthesia injection according to the present invention.
FIG. 3 is an elevational view of the front panel of a drive unit of the invention during one phase of operation.

As shown in FIG. 1, the injection of the present invention requires the practitioner to first locate the needle tip 10 near the target tissue, that is for example, near the PDL (periodontal ligament) 12 between the subject's tooth root 14 and the subject's jaw bone 16, and to physically guide the needle tip along the tissue target. This is achieved using real-time dynamic pressure sensing technology in the form, for example, of the apparatus generally designated 20 in FIG. 2, and the principle that tissues in the body have varying densities. The periodontal ligament, for example, has an interstitial pressure range that is unique to the surrounding tissues, namely bone 16, the tooth root 14, and attached and unattached gingival tissues 18.

Once the needle tip 10 is located in the proper space, the apparatus 20 provides real-time confirmation that the needle tip has not moved outside the tissue target during administration. In addition to location, the apparatus of the invention provides pressure-sensing feedback to ensure that no blockage of the needle by obstruction or tissue clogging has occurred. This dynamic pressure sensing can also alert the practitioner if leakage occurs, which can sometimes be a result of poor needle placement, insufficient hand pressure on the handpiece or internal leakage of the cartridge or tubing to be described in greater detail later in this disclosure. The invention informs the practitioner if a potential loss of pressure has occurred from any of the scenarios described.

By using the present invention, the anesthetic dosage administered can be greater than with previous intraligamentary injection techniques. This is due to both the moderate pressures applied and a controlled flow rate of administration.

Data considered by the inventor indicates that the volume of injection solution is not limited via the intraligamentary route when performing the intraligamentary injection of the present invention. Therefore, the recommended dosage of anesthetic solution ranges from 0.9 ml (for single rooted teeth) to 1.8 ml (for multi-rooted teeth) when using a 2% concentrated local anesthetic solution.

When using a 4% concentrated drug, such as Articaine Hyrdochloride, half the dosage is recommended, i.e. 0.4 ml (for single rooted teeth) to 0.9 ml (for multirooted teeth). The practitioner should understand that the volume of anesthetic is related to the duration of anesthesia, and plan according to individual procedural needs. Re-dosing during treatment is possible as well with the injection technique of the invention.

Performing the Injection Using the Hardware:

Drive unit 22 is portable and about the size of a small cable modem. The handpiece handle 24 is part of a single-use disposable handpiece assembly. The drive unit 22 is powered by a standard AC electrical connection. The unit illustrated, for example, has a power cord 36 with a unit plug 38 for being plugged into the back of unit 22, and a wall plug 40 for an AC wall socket used in the United States, for example.

The single-use sterile, disposable handpiece assembly includes the handle 24, the micro-bore tubing 26, and an anesthetic cartridge holder 34 that accepts any standard dental anesthetic cartridge 28. Any standard medical needle 30 can be attached to the handpiece for use. Typically, a 30-gauge or 27-gauge ½ inch luer-lock needle 30 is attached to the handle 24 to perform the intragamentary or PDL injection according to the present invention.

The drive unit 22 has three basic modes of operation:

a. STA mode—a one-speed mode (0.005 ml/sec flow rate);

b. Normal mode—a two-speed mode (0.005 ml/sec and 0.03 ml/sec);

c. Turbo mode—a three-speed mode (0.005 ml/sec, 0.03 ml/sec and 0.06; and ml/sec).

When performing the intraligamentary injection only the STA mode is used. All injection rates are controlled by the practitioner using a foot-control or pedal 42 connected to the drive unit 22 by a conduit 44 plugged below a front panel 50 of the unit, at a foot control receptacle 46.

It is noted that for all modes of operation and for the acquiring of the pressure signals and generation of the perceptible signals, an on-board computer is included in unit 22 which has been programmed using techniques and technologies that are currently available to the person of ordinary skill in this art. Additional details are also available from the assignees previous patents and published patent applications, as well and the co-pending and co-invented U.S. Patent Application US 2006/0122555.

STA-Mode:

To perform the injection, the subject or patient is seated in the supine position. The practitioner selects the appropriate anesthetic solution for the desired result and places the cartridge 28 into the cartridge holder 34 of the handpiece assembly. The patient should be informed that they will hear audible sounds from the system throughout the procedure.

The cartridge holder 34 is then attached to the drive unit 22 by plugging the lower end of holder 34, which has a pair of opposite tabs 35, into a cartridge holder socket 52 at the top of the unit. The holder 34 is then rotated about 90 degrees on its axis to engage the tabs 35 into matting slots inside socket 52. This rotation both locks the cartridge holder with its cartridge in the socket, and closed a switch in socket 52 that performs other monitoring and safety functions. See U.S. Pat. No. 6,132,414, for example, for details on the cartridge holder and how it receives and punctures the cartridge for releasing the anesthetic liquid.

The drive unit 22 has previously been activated by depressing a power button 54 on the rear of the unit. This lights a power indicator lamp 56. An STA button 58 is then pressed to activate this mode of operation and the STA mode lamp 60 lights as well. FIG. 3 shows the condition of the indicators on panel 50 during this time.

The unit 22 will then automatically remove the air from the micro-tubing 26 of the handpiece and needle. This purge cycle is indicated by lighting of an Auto Purge/Retract indicator lamp 62 and is achieved by a plunger 64 that is linearly driven up into the cartridge 28 in a controlled manner and by a set amount to inject the liquid anesthetic from the cartridge, along the tubing and out from the needle tip 10 in a manner that is well recognized by the practitioner to indicate that no air is left in the handpiece assembly. At this point, a remaining cartridge quantity indicator 66 shows the cartridge 28 to be full by having all or almost all of it divisions lit. A top-most, over-full division may have been lit originally, and then extinguished to show some use of liquid for the purge cycle.

Holding the handpiece 24 with a pen-like grasp, the practitioner will place the needle into the gingival sulcus of the tooth to be anesthetized as shown in FIG. 1. Simultaneously, the practitioner will activate a first selected liquid flow rate (e.g. at least 0.002 ml/sec or about 0.005 ml/sec) by depressing the foot control 42. It is important to gently and slowly advance the needle tip 10 within the sulcus, as if it is a periodontal probe. Using a finger-rest to control the movement of the needle is highly recommended as this will allow the practitioner to carefully control and stabilize needle movements. It is also recommended that the bevel of the needle face the root surface and that the needle be angled approximately 30-45 degrees to the long axis of the tooth.

As the needle is introduced through the tissues, the system of the present invention provides continuous audible and/or visual feedback to assist the practitioner. The unit 22 has the visual pressure sensing scale 32 (i.e. gauge) on the front 50 of the unit which is made up of a series of LED lights that may, for example be orange, yellow and green. Orange lights at the left which are shown lit in FIG. 3, indicate minimal pressure, yellow lights or divisions in the middle of scale 32 indicate mild pressure measurements, and a green light toward the right indicates moderate pressures indicative of the intraligamentary (PDL) tissue.

The auditory feedback is composed of a series of sounds with a pressure sensing scale composed of ascending tones to also guide the practitioner. When the practitioner hears the ascending sequence, this indicates that the pressure is raising. When the periodontal ligament is identified as a result of the instantaneous real-time pressure becoming equal to the minimum desired pressure, the practitioner will initially hear the letters "P-D-L" actually spoken by the unit over the speaker, indicating that the correct needle position has been achieved.

The auditory signal can be continuous, but it is also be noted to be specific as to the response of an absolute value of pressure, such as the announcement of "P-D-L". The same thing can be done when the STA detects the Ligamentus Flavum in which the unit would announce "Flavum" and then when the specific pressure of the Epidural space is identified it would say "EPI-Dural-Space".

Feedback to the user is not only auditory at the absolute pressure value in the preferred embodiment, but it is also visual as we see a distinct color LED signifying the PDL tissue has been reached. The minimum, desired or threshold pressure is an absolute value but it may lie within the discovered range for that tissue. The set point for the feedback perceptible signal may be higher or lower within that range depending on different factors, but it is the absolute pressure that is being sought.

For example STA injection works in the range from, for example, about 250 to 450 psi, because as soon as the absolute value of 250 psi (minimum threshold pressure or absolute pressure value is reached) the STA announces that the location or tissue has been identified. The apparatus and method of the invention is not looking for a range although it continues to announce "P-D-L" through the range. It relies on detecting the absolute value to identify the tissue. As stated, the STA could be silent until it reaches that tissue, but in preferred form it is informing the user that the pressure is increasing toward the desired absolute pressure value instead.

Clinical use of the system has found that it is not uncommon to have to re-position the needle to find the optimum position within the intraligamentary tissues. This "searching" is guided by real-time dynamic pressure sensing feedback and is what allows a practitioner to develop a high degree of predictability and accuracy when performing this injection. The dental "blind" syringe approach to needle position is now transformed into a systematic method to finding the correct needle-to-intraligamentary position using the present invention. All of this can be performed in a virtually painless and unobtrusive manner to the patient.

The real-time feedback of the device also informs the practitioner to the proper hand-pressure to be applied upon THE WAND (a registered trademark of the assignee of the subject application, Milestone Scientific, Inc.) handpiece. Heavy or forceful pressure on the handpiece can block the flow of anesthetic solution. This blockage will be detected by the system and an "over-pressure" condition will occur. An "over-pressure" condition is when pressures exceed the maximum pressure. The STA Single Tooth Anesthesia System (also a register trademark of the assignee) drive unit will sound an auditory and visual alarm, e.g. a louder sound or the lighting of the last red LED at the right hand end of scale 32 or the "occult" of LED in a flashing sequence to indicate that an over-pressure condition has occurred. The practitioner can then restart the injection. It might be necessary to re-position or move the needle to a new location.

The real-time feedback of the device also informs the practitioner to the proper hand-pressure to be applied upon THE WAND handpiece. Heavy or forceful pressure on the handpiece can block the flow of anesthetic solution. This blockage will be detected by the system and an "over-pressure" condition will occur. An "over-pressure" condition is when pressures exceed the maximum pressure. The STA drive unit will sound an auditory and visual alarm, e.g. a louder sound or the lighting of the last red LED at the right hand end of scale 32 or the "occult" of LED in a flashing sequence to indicate that an over-pressure condition has occurred. The practitioner can then restart the injection. It might be necessary to re-position or move the needle to a new location.

If too little hand-pressure is applied when establishing the needle-to-intraligamentary relationship then a proper seal between the needle and the intraligamentary tissue cannot be established. This leads to insufficient pressure or leakage of the anesthetic solution into the patient's mouth. The system with the inventive technology will detect this before it can be visually seen by the practitioner by used of the instantaneous pressure sensing and feedback signals, that, in this case, are not raising in the expected manner but may be fluctuating to indicate that the real-time, instantaneous pressure is rising and falling in an uncontrolled manner.

This prevents the typical bitter taste of anesthetic to the subject, because the leakage was not detected in a timely manner when using a mechanical dental syringe. More importantly, the invention and its feedback system establishes how the practitioner should apply consistent hand-pressure to the handpiece. This becomes another attribute making the intraligamentary injection of the present invention a predictable and easy alternative when compared to injections and devices that cannot provide this information.

The practitioner should use his or her own judgment as to the anesthetic drug selection and volumes used. The following information serves only as a guideline, and practitioners are advised to refer to the appropriate drug manufacturers for specific guidelines. In addition, practitioners are advised to review the current dental literature and dental textbooks for guidance on recommended dosages and drug recommendations.

When using 2% Xylocaine Hydrochloride or other local anesthetics formulated with a 2% concentration, the following recommendations are made. A drug volume of 0.9 ml is recommended for single rooted teeth. A drug volume of 1.8 ml is recommended for multi-rooted teeth. When using 4% Articaine Hydrochloride or other local anesthetics formulated with a 4% concentration, the following recommendations are made. It is strongly recommended with using 4% Artcaine hydrochloride that a 1:200,000 vasoconstrictor concentration be used. A drug volume of 0.4 ml is recommended for single rooted teeth and a drug volume of 0.9 ml is recommended for multi-rooted teeth.

The intraligamentary injection of the invention provides a unique, single tooth injection technique that provides a level of safety, comfort and predictability previously unattainable.

The invention provides the practitioner with at least three distinct benefits that cannot be achieved using a standard dental syringe, the pistol-grip high-pressure syringe, or other CCLADS systems. First, the invention provides the practitioner with an objective means to determine tissue compliance and thereby determine the tissue type into which the needle is inserted. Second, the system provides the practitioner with objective, continuous, real-time pressure feedback data ensuring that the prescribed moderate pressure range is maintained within the injected tissues. And thirdly, the invention provides the practitioner with objective real-time information as to the occlusion of a needle and/or the loss of pressure resulting from intra-oral anesthetic solution leakage.

The uniqueness of the inventive apparatus and method is the ability to provide important clinical feedback in a real-time fashion, thus allowing adjustments and confirmations to be made as determined by the practitioner. This technology simplifies the process of intraligamentary injections by providing practitioners with a new, interactive injection system. However, it should be understood that the procedure still requires users to have an in-depth knowledge of basic anatomy, basic technique, and a full understanding of local dental anesthesia.

An intraligamentary injection, performed with the invention, eliminates previous subjectivity regarding correct needle position and leads to a high level of confidence, and success in single tooth dental anesthesia.

Although the intraligamentary injection is disclosed as an example of the invention, other selected tissues that can be injected using the present invention. One further example is the epidural space which is a part of the human spine that is very close to the spinal cord, lying just outside the dura mater. Using an epidural catheter both anesthesia and analgesia can be administered. Each selected tissue type will have its own desired pressure for optimal effectiveness of the drug to be administered so that the advantages of feeding a perceptible signal to the practitioner that returns information corresponding to that desired pressure is clear.

As noted above, the apparatus and method of the present invention relies upon an absolute or specific objective value of the real-time, instantaneous pressure at the needle tip to identify the desired target location, i.e. specific tissue. The method described herein requires an objective, not a relative pressure value, in order to accurately identify the intended tissue structure such as the PDL tissue (i.e. identified between 250 psi to 450 psi). One cannot rely upon a relative pressure change to identify the PDL tissue, but must first quantify what is the specific interstitial tissue resistance (i.e. exit-pressure) at a specific flow-rate.

Another example of specific tissue pressure and injection that can be used according to the present invention is the Attached Gingival injection or PI—Palatal Injection which was shown in the Hochman et al. study identified above to have mean pressure of 68.18 psi and a range of about 50 to 75 psi of objective or absolute pressure value to detect that the apparatus and method has identified the correct location of the needle tip.

The Ghelber et al. article also identified above also gives specific exit-pressure values for the Ligamentum Flavum, as well as two additional tissues in the abstract. These are specific values, not relative values to identify the Epidrual space.

Normal Mode:

To use the unit 22 of the present invention for a normal mode of operation, a selector button 68 is pressed once. This causes a normal mode indicator LED or lamp 70 to light.

In this mode of operation, the purge cycle will occur when a new cartridge in installed. After this is done, pressing the foot controller or pedal 42 down by a small amount will cause plunger 64 to move into the drug cartridge at a slow speed for discharging a first lower rate of drug, e.g. 0.005 ml/sec. Pressing the pedal down more to a second position will increase the plunger speed and discharge at a second greater speed, e.g. 0.03 ml/sec.

Turbo Mode:

Turbo mode is started by pressing selector button a second time. Turbo mode indicator lamp 72 lights and foot pedal 42 has three depressed positions corresponding to three plunger speeds and three corresponding flow rates, e.g. 0.005 ml/sec, 0.03 ml/sec and 0.06 ml/sec. Turbo mode can be used for quickly discharging the remainder of drug in a cartridge that is no longer needed for a patient.

Other Features of the Invention:

A audible volume control button 74 having upper and lower functional ends is used to respectively increase and decrease the volume of the audile feedback signal from speaker 23.

An aspiration initiation button 76 is pressed to initial an aspiration cycle feature. When the feature is enabled the device will automatically aspirate when the users foot is removed from the foot control during drug infusion. When the feature is disabled the user can remove his/her foot from the foot control and then the device will generally stop infusion with no further plunger movement. Aspiration indicator 78 will light and the computer in unit 22 is programmed to pull slightly back on plunger 64. Since plunger 64 has an O-ring 65 around its end that seals inside cartridge 28, when plunger 64 is pulled back, the partial vacuum in the space between the upper end of plunger 64 and the lower end of the usual drug driving piston in cartridge 28, caused the piston to also move back, thus withdrawing fluid from the patient at the injection site. Since the inside diameter of tubing 26 is small, very little aspiration movement is needed to insure that no blood vessel has been invaded.

Unit 22 also includes an auto purge and retract button 80 that is pressed momentarily to initial an automatic purge only, or pressed and held for a period of seconds to initiate a full retraction of plunger 64 from the cartridge in anticipation of removing the cartridge, for example after it have been spent.

A multi-cartridge button 84, having a corresponding multi-cartridge indicator 84, is pressed momentarily to initiate a multi-cartridge mode that allows a new cartridge to be installed but not be subjected to an automatic purge cycle. This is to avoid purging the handpiece assembly when it is already filled with drug from the previous cartridge. Button 84 is pressed and held for a period of seconds to initiate a verbal training mode which causes the unit to verbally describe and state each operation and each cycle over speaker 23, for training purposes. For example, when the Select button 68 is pressed to initiate the Normal Mode with two flow rates available, the voiced will say "Normal mode active," and when the pedal 42 is pressed to the first low rate position, the voice will say "Low flow rate initiated." Like verbal messages will be stated for each mode of operation and for each phase of each mode to help train and familiarize the busy practitioner in an effective, memorable, and "on-the-job" manner.

Unit 22 also includes a pair of opposite wings 86 which each contain a handpiece tip holder 88 shaped to receive and lined with resilient high-friction material to hold the tip of the handpiece handle 24 like a pen holder for convenience.

Another characteristic of living tissue that can be used according to the present invention to improve the effectiveness of an injection is its compliance.

That the device of the invention can be programmed for a specific tissue based on tissue compliance. Tissue compliance can be qualified as change of volume over change in pressure. When the specific compliance of a tissue has been identified then the device will alert the practitioner when that tissue has been reached by the point of the needle being manually guided by the practitioner.

Compliance denotes a change of volume required during the change in pressure to allow identification of the desired tissue. Compliance differs from tissue resistance or interstitial pressure which can be measured statically, while the compliance of the tissue requires a dynamic condition to be in place in which there is a change in volume to change in pressure. With this understanding the pressure sensor of the system and method of the invention can be used to guide the practitioner's hand. The change in volume parameter adds is addressed by the fluid flow which must be occurring simultaneously with the change in pressure to allow for the tissue identification.

As with the embodiment of the invention that indicates when the selected tissue has been reached by feeding back to the practitioner a perceptible signal that indicates the desired pressure has been reached, the pressure measurement for the compliance identification technique, relies on the instantaneous exit pressure of the fluid, that is, the pressure of the fluid at or near the very point of the needle.

The invention can also be used for guidance or tactile control of the handpiece which is different then actual tissue identification, i.e. pressing harder or holding lighter. This can be independent to identifying the target tissue.

The pressure sensor or calculator for this embodiment of the invention thus, is a pressure sensor for sensing the instantaneous pressure comprising means for determining change in pressure ($P^2-P^1=\Delta P$) over a defined time period, a means for determining a change in volume ($V^2-V^1=\Delta V$) over a defined time period, and a means for determining the compliance of the tissue based on a change in volume to over a change in pressure, the calculated compliance being compared to a defined compliance for a given anatomic location or structure and the practitioner being guided to a specific target tissue based on identification of specific compliance.

The unit 22 also has a drainage feature for draining drug from the bottom of the unit. Mounting screw 124 in FIG. 4 is a mounting screw on the base of the unit which also allows mounting and securing of the unit near the practitioners work space.

It is noted that terms used in this disclosure such as cartridge, cassette and the like, are meant to have their broadest possible meaning. For example the term cartridge is meant to include any container or vessel for containing the liquid to be injected.

While specific embodiments of the invention have been shown and described in detail to illustrate the application of the principles of the invention, it will be understood that the invention may be embodied otherwise without departing from such principles.

What is claimed is:

1. An apparatus for a practitioner to administer a controlled injection of a dental anesthetic drug into intraligamentary tissue of a subject, the apparatus comprising:

a drive unit for supplying the drug at least one flow rate;

a handpiece for being held by the practitioner, the handpiece being connected to the drive unit by a flexible tube for receiving the drug, the handpiece carrying an injection needle to be inserted into the subject near the intraligamentary tissue of the subject, the injection needle having a tip for passing the drug to the subject at an instantaneous and at an absolute pressure that is at the tip of the injection needle, and that varies due to a placement of the needle tip in the subject, there being a minimum threshold pressure of about 200 to 500 psi and an absolute pressure which is desired for administering the drug to the intraligamentary tissue;

a computer connected to the drive unit and programmed for operating the drive unit for supplying the dental anesthetic drug to the injection needle at a selected flow rate while the practitioner holds the handpiece, the tip of the needle adapted to be inserted into the subject at a location near the intraligamentary tissue of the subject for passing the drug to the subject near the intraligamentary tissue at the instantaneous and absolute pressure that is at the tip of the needle and that varies in real-time as a function of the intraligamentary tissue and a placement of the tip of the needle;

a pressure sensor connected to the computer for sensing or calculating the instantaneous pressure on a real-time basis;

a sound generator connected to the computer, the computer being programmed for driving the sound generator for supplying a perceptible auditory ascending signal to the practitioner that indicates when the instantaneous pressure is rising toward the minimum threshold pressure, for guiding movement of the placement of the tip of the needle by the practitioner at least until the minimum threshold pressure has been reached;

the computer being programmed for driving the sound generator for supplying a perceptible auditory specific signal to the practitioner that indicates when the instantaneous pressure has reached the minimum threshold pressure which indicates that the practitioner has moved the tip of the needle into the intraligamentary tissue and so that after the perceptible auditory specific signal is supplied, the practitioner maintains the tip of the needle in the intraligamentary tissue for supplying a selected dosage of the drug to the intraligamentary tissue at the selected flow rate; and the computer also being programmed for driving the sound generator for notifying the practitioner by generating a perceptible auditory signal when the instantaneous pressure declines or fluctuates before reaching the minimum threshold pressure.

2. The apparatus according to claim 1, including a visual scale connected to the computer and the computer being programmed to drive the visual scale for supplying to the practitioner a visual signal which includes a plurality of signals that correspond to different real-time values for the instantaneous pressure before it has reached the minimum threshold pressure, and at least one visual signal that indicates that the instantaneous pressure has reached the minimum threshold pressure.

3. The apparatus according to claim 1, wherein the computer is programmed for driving the sound generator for supplying to the practitioner a further perceptible signal when the instantaneous pressure is above a selected over-pressure to indicate to the practitioner that an undesirable over-pressure condition has occurred.

4. The apparatus according to claim 1, wherein the minimum threshold pressure is in the range of about 200 to 500 psi and the selected flow rate is at least about 0.002 ml/sec.

* * * * *